United States Patent [19]
Barri et al.

[11] Patent Number: 4,585,641
[45] Date of Patent: Apr. 29, 1986

[54] PROCESS FOR PRODUCING CRYSTALLINE GALLOSILICATES

[75] Inventors: Sami A. I. Barri, London; Dennis Young, Staines, both of England

[73] Assignee: The British Petroleum Company P.L.C., London, England

[21] Appl. No.: 734,754

[22] Filed: May 15, 1985

Related U.S. Application Data

[63] Continuation of Ser. No. 527,789, Aug. 30, 1983, abandoned.

[30] Foreign Application Priority Data

Sep. 4, 1982 [GB] United Kingdom ................. 8225278

[51] Int. Cl.$^4$ ............................................. C01B 33/20
[52] U.S. Cl. .................................... 423/331; 423/326; 423/332; 502/61
[58] Field of Search .............................. 423/326–333; 502/60, 61, 62, 71, 77

[56] References Cited

U.S. PATENT DOCUMENTS

| 3,702,886 | 11/1972 | Argauer et al. | 423/328 |
| 3,709,979 | 1/1973 | Chu | 423/328 |
| 3,832,449 | 8/1974 | Bosinski et al. | 423/328 |
| 4,392,003 | 7/1983 | Kolombus et al. | 585/661 |

FOREIGN PATENT DOCUMENTS

| 0057049 | 8/1982 | European Pat. Off. | 423/329 |
| 0077624 | 4/1983 | European Pat. Off. | 423/328 |
| 2023562 | 1/1980 | United Kingdom | 423/326 |

Primary Examiner—Edward J. Meros
Attorney, Agent, or Firm—Brooks Haidt Haffner & Delahunty

[57] ABSTRACT

This invention relates to crystalline gallosilicates having the following composition in terms of the mole ratios of the oxides:

$$0.9 \pm 0.25 M_{2/n}O:Ga_2O_3:xSiO_2:yH_2O.zQ$$

wherein M is at least one cation having a valence n, x is at least 10, y/x is from 0 to 30, Q is a template used in the synthesis of the gallosilicate and z/x is 0–20, wherein the gallosilicate in the organic free hydrogen-form has an X-ray diffraction pattern substantially as set forth in Table A of this specification. The gallosilicates may be used, whether or not impregnated and/or ion-exchanged, admixed, supported or bound, for catalyzing a reaction selected from alkylation, dealkylation, dehydrocyclodimerization, aromatization, transalkylation, isomerization, dehydrogenation, hydrogenation, cracking, hydrocracking, cyclization, oligomerization, polymerization, conversion of carbon monoxide/hydrogen mixtures to hydrocarbons and dehydration reactions.

11 Claims, No Drawings

PROCESS FOR PRODUCING CRYSTALLINE GALLOSILICATES

This application is a continuation, of application Ser. No. 527,789, filed 8/30/83, abandoned.

The present invention relates to novel gallosilicates and to methods of preparing the same. More particularly, this invention relates to novel crystalline gallosilicates having catalytic properties, to methods of preparing the same, and hydrocarbon conversion therewith.

Zeolites are well known natural and synthetic compositions. Many of them have been demonstrated to have catalytic properties for various types of hydrocarbon and related reactions. Zeolites can be defined as ordered porous crystalline aluminosilicates having a framework structure sufficiently open to accommodate at least water molecules. Such structures generally contain a regular array of small voids interconnected by channels or pores. The dimensions of the voids and channels can range from those of water to those of quite large molecules. For a given framework structure, the dimensions of the voids and channels are limited to a small number of values, which can vary from structure to structure. Thus these structures are capable of absorbing molecules of certain dimensions while rejecting those of dimensions larger than a critical value which varies with structure. This has led to zeolites being used as molecular sieves. Zeolites belong to a class of materials that can be termed tectoaluminosilicates which comprise (in addition to zeolites) felspars and felspathoids. They can be defined as having a framework structure consisting of a rigid regular three dimensional network of $SiO_4$ and $AlO_4$ tetrahedra in which the tetrahedra are cross-linked by sharing the oxygen atoms. All oxygen atoms are shared, thus the ratio of total aluminium and silicon atoms to oxygen atoms is 1:2. The inclusion of aluminium in the framework leads to a net negative charge which is balanced by the inclusion in the crystal of an electrochemical equivalence of cations, for example alkali metal, alkaline earth metal, hydrogen or ammonium cations or mixtures thereof. This can be expressed by a formula in which the ratio of Al to the number of the various cations such as Ca/2, Sr/2, Na, K, Li or generally M/n (where n is the formal oxidation state of the cation) is equal to unity. Additionally in zeolites, but not in felspars and some felspathoids, the framework is sufficiently open to accommodate water molecules as well as cations. This enables these cations to be exchanged in their entirety or partially by other cations using ion-exchange techniques in a conventional manner. These materials an exhibit specific affinities for specific cations and can thus be used as selective ion-exchangers. By means of ion-exchange, it is possible to vary the size of the pores in a given crystalline zeolite material, modifying its molecular sieve properties. Also by means of ion-exchange the catalytic properties of these materials can be altered. In addition to the framework and charge-compensating cations, zeolites can contain other materials such as water and organic molecules, (hydrated) salts and oxides of eg Na, Al and Si introduced during synthesis, or formed or added during subsequent treatments. Zeolites are best characterised according to framework structure type, ie on the topology of the framework, irrespective of composition, distribution of different tetrahedral atoms, cell dimensions and symmetry. A code consisting of three capital letters has been adopted for each known structure type following the recommendations by IUPAC on zeolite nomenclature ("Chemical Nomenclature, and Formulation of Compositions, of Synthetic and Natural Zeolites," IUPAC yellow booklet, 1978) and a compilation of 38 known zeolite structure types has been published by The Structure Commissiion of the International Zeolite Association ("Atlas of Zeolite Structure Types", by Meier, W. M. and Olsen, D. H. (1978), distributed by Polycrystal Book Service, Pittsburgh, Pa, USA). In addition to the groups classified by known structure type, there is a further group of crystalline zeolite materials whose X-ray diffraction patterns, sorption, ion-exchange and related properties indicate that they do not have known structure types but appear to have new, as yet undetermined structure types. An example of such a material is the novel porous crystalline aluminosilicate designated Theta-1 and described in our published copending European patent specification No. 0057049.

Zeolites (and other tectoaluminosilicates) belong to a larger class of materials that can be termed tectometallosilicates which can be defined in the same way as tectoaluminosilicates except that the aluminium is replaced by a range of elements, which includes, it is claimed, Ti, Zr, V, Cr, Mo, Mn, Fe, Co, Rh, Ni, Zn, B, Al, Ga, Ge, Sn, As and Sb, but in some cases the claimed materials have not been well characterised. In some cases (where the element has the same formal oxidation state as Si ie +4) the resultant framework is electroneutral and the resultant materials resemble crystalline silicas. In other cases there is a resultant framework negative charge which must be compensated by cations as in tectoaluminosilicates. In some cases the materials have porous frameworks like those of zeolites or porous crystalline silicas which they therefore resemble.

A number of porous crystalline tectogallosilicates have been claimed (for example see Barrer, R. M., Hydrothermal Chemistry of Zeolites, Academic Press, London, 1982 pp 282–282). Of special interest here are high silica porous crystalline tectogallosilicates: (defined as having a $SiO_2:Ga_2O_3$ molar ratio of at least 10). For example, UK patent application No. 2053960A describes the hydrothermal synthesis of MFI-type gallosilicates from gels containing tetrapropylammonium cations as template. By "template" is meant throughout this specification a chemical agent which encourages crystallisation to proceed towards a particular framework structure or structures.

Our copending European application published under No. 0057049 describes a process for preparing crystalline aluminosilicates, designated as Theta-1 and having a characteristic X-ray diffraction pattern substantially different to that of MFI-type aluminosilicates, by crystallising a mixture containing a source of silica, a source of alumina, a source of alkali metal and a nitrogenous organic base which is for instance a di- or trialkanolamine.

It has now been found that a novel crystalline gallosilicate, designated Gallo-Theta-1, can be produced by crystallisation from a mixture containing a source of gallia, a source of silica, a source of alkali metal(s), water and a template such as an organic or inorganic nitrogen-containing base, such as eg diethanolamine or ammonia.

Accordingly, the present invention provides novel crystalline gallosilicates having the following composition in terms of the mole ratios of the oxides:

$$0.9 \pm 0.25 M_{2/n}O : Ga_2O_3 : xSiO_2 : yH_2O : zQ$$

wherein M is at least one cation having a valence n, x is at least 10, y/x is from 0 to 5, Q is a template used in the synthesis of the gallosilicate and z/x is 0–20, wherein the gallosilicate in the organic-free hydrogen-form has an X-ray diffraction pattern substantially as set forth in Table A of this specification.

Thus the gallosilicates of the present invention have a Theta-1-type structure as described in our European Patent specification No. 0057049.

By the term "organic-free hydrogen-form" is meant here and throughout this specification that the gallosilicate has been rendered substantially free of organic material introduced during synthesis or subsequent treatments, and the cation M is hydrogen. The gallosilicates prepared from organic bases contain organics as synthesised and these can suitably be removed by calcination in air. The gallosilicates prepared from ammonia do not contain organics as-synthesised. Therefore, in such a case, an organics removal step such as calcination in air is not essential.

The $H_2O$ content "y" of the gallosilicate is the water of hydration and will depend, within the ratios set out above, upon the conditions under which it is dried, calcined, subjected to further aqueous treatments or combinations thereof after synthesis. The $H_2O$ content "y" does not include water which may be notionally present when the cation M is hydrogen.

The 'template' as defined above is a chemical agent, e.g. an organic or inorganic base which encourages crystallisation to proceed towards a particular framework structure or structures.

The content "z" of template "Q" in the gallosilicate will also depend upon the conditions under which it is washed, calcined or subjected to further aqueous treatments or combinations thereof after synthesis, and also on the synthesis parameters of the gallosilicate, particularly the proportion of Q present in the original hydrogel. The molar ratio of the template Q to silica, i.e. z/x is preferably 0–5 in the gallosilicate as synthesised. The template content is usually highest for the "parent" gallosilicate. Complete removal of the template, if present, is usually only possible by thermal or oxidative degradation or both.

By the "parent" gallosilicate is meant throughout this specification the product of synthesis and washing and optionally drying as hereinafter described.

The cation M in the gallosilicate may be selected from $H^+$, ammonium, alkali metal cations, alkaline earth metal cations, organic nitrogen containing cations, aluminium cation, gallium cation and mixtures thereof.

The cations present in the gallosilicate may be replaced using conventional ion exchange techniques either wholly or partially by other cations e.g. hydrogen ions or metal cations.

The organic-free hydrogen-form of the gallosilicate may be produced by known methods such as exchange with hydrogen ions or with ammonium cations followed by one or more calcinations or a combination of the two followed by one or more calcination stages, if the gallosilicate still contained ammonium ions.

The gallosilicates according to the present invention, designated herein as "GalloTheta-1", have in their organic-free hydrogen form an X-ray diffraction pattern shown in Table A below. The specific values in the Tables were determined using copper K-alpha radiation and a computer step scan.

The peak heights, I, and their position as a function of 2 theta, where theta is the Bragg angle, were read from the spectrometer output. From this output the relative intensities $100 \times I/I_o$, where $I_o$ is the intensity of the strongest peak, and d the interplanar spacing in Å, corresponding to the recorded peaks were calculated.

It will be understood by those skilled in the art that the X-ray diffraction pattern of gallosilicates may vary in the values of $I/I_o$ and the d-spacing depending for example upon whether the sample being examined is calcined or uncalcined, upon the temperature of calcination, upon the nature of the cation present in the gallosilicate, the mole ratio of silica to gallia, and the particle size of the gallosilicate.

The gallosilicate is suitably produced by mixing a source of silica, a source of gallia, a source of alkali metal(s), water and an organic or inorganic nitrogen containing base until a homogeneous gel is formed and crystallising the gel at a temperature above 70° C.

The silica to gallia mole ratio in the initial mixture is at least 10:1. The silica to gallia mole ratio is suitably greater than 40:1 and the free alkali metal(s) hydroxide to water mole ratio, defined as:

$$\frac{[(\text{Number of moles of total alkali metal(s)}) - (\text{Number of moles of alkali metal(s) required to convert gallia present to alkali metal gallate(s), ie } MGaO_2)]}{\text{Number of moles of water present}}$$

is suitably greater than $2 \times 10^{-3}:1$. The silica to gallia mole ratio is preferably in the range 60:1 to 500:1 and the free alkali metal(s) hydroxide to water mole ratio is preferably in the range $2 \times 10^{-3}:1$ to $8 \times 10^{-3}:1$. Similarly the mole ratio of silica to free alkali metal(s) hydroxide may suitably be greater than 1:1, preferably between 5:1 and 80:1, most preferably between 5:1 and 40:1, and the mole ratio of water to silica may suitably be less than 100:1, preferably between 6:1 and 30:1, even more preferably between 9:1 and 30:1.

Using diethanolamine as the nitrogen containing organic base, GalloTheta-1 substantially free from other crystalline gallosilicates, e.g. those with MFI-type structures (as defined in the "Atlas of Zeolite Structure Types" referred to above), can be produced at a silica to gallia mole ratio greater than 60:1 in the initial mixture. At a silica to gallia mole ratio in the range 25:1 to 50:1 in the initial mixture MFI gallosilicates substantially free of GalloTheta-1 may be produced. It must be noted that this is an improvement on the MFI gallosilicates more conventionally produced using tetraalkyl ammonium salts in that the alkanolamines are less expensive and less toxic.

In preparing the gel, sources of silica which may be used include for instance sodium silicate, silica hydrosol, silica gel, silica sol and silicic acid. It is preferable to use an aqueous colloidal dispersion of silica particles, eg the Ludox (Registered Trade Mark) varieties manufactured by DuPont.

The alkali metal(s) used in the initial mixture may similarly be the inorganic salts containing these metals, their oxides and their hydroxides. Sodium is the preferred alkali metal.

The nitrogen containing base used may be selected from ammonia or organic bases such as alkanolamines. Di- and tri-ethanolamines and their decomposition products under the synthesis conditions are preferred.

The sources of gallia used may include for instance inorganic gallium salts such as the oxides, hydroxides and gallates. The source of gallium is preferably activated by the addition of aqueous alkali hydroxides and a nitrogen base to the appropriate proportion of freshly precipitated gallium hydroxide, and then the source of silica is slowly added to the activated gallium hydroxide.

It has been found that if a non-activated source of gallia is used, for example, gallia which is an aged and then dried gallium hydroxide precipitate, an amorphous gallium-containing material is produced under the hydrothermal conditions used to produce galloTheta-1 from an activated gallium hydroxide. This appears to be a function of the template rather than the structure. Thus it has been found that a diethanolamine-containing gel (that would give an MFI-type gallosilicate on hydrothermal synthesis if an activated gallium hydroxide had been used) also gives only an amorphous product if an aged and then dried gallium hydroxide precipitate is used instead. Conversely, it has been found that an MFI-type gallosilicate can be prepared either from an activated gallium hydroxide or from a dried, aged gallium hydroxide sample if tetrapropylammonium hydroxide is used as template.

The reason for this would appear to be that the gallium species added to the initial gel has to be highly dispersed, e.g. as an aqueous gallate solution or as a highly dispersed hydroxylated sol, in order for a crystalline tectogallosilicate to form from that gel. Templates such as diethanolamine used in the synthesis of galloTheta-1 are only weakly basic and cannot themselves easily activate the gallium species present. Stronger bases such as tetrapropylammonium hydroxide can act not only as a template but can also activate the gallium species present. All materials used herein as templates for galloTheta-1 are weakly basic.

The gallosilicate, GalloTheta-1, is suitably prepared by forming a mixture of all the reactants, by simply mixing them together while maintaining the mixture suitably at a temperature between 0° to 100° C., preferably between 20° and 60° C., until a homogeneous gel is formed and crystallising the gel so-formed at a temperature above 70° C., preferably between 100° and 220° C. for a period of at least 2 hours, preferably for 6 to 240 hours. The optimum crystallisation period can vary and may depend upon such factors as the temperature, agitation, pH, gel composition and seeding. The mixing and digestion of the ingredients is suitably carried out under autogenous pressure although the pressure can be further increased by pressurisation with a suitable gas, eg nitrogen. It is preferable to agitate the mixture during the crystallisation stages. It is preferable that the silica source is added to the other reagents in such a manner as to commence gelation at a relatively high pH.

The product obtained in this manner contains cations which may be hydrogen, alkali metal(s), gallium, or organic nitrogen containing cations or any combination thereof.

The cations in the product may be converted to hydrogen to give rise to the hydrogen-form of the product. This may be achieved by techniques known to those skilled in the art, e.g. (a) ammonia exchange followed by calcination, (b) acid exchange or a combination of (a) and (b).

The product or the hydrogen-form thereof may also be loaded with with additional metals or oxides suitable for imparting a specific type of catalytic activity. The loading may be achieved by conventional ion-exchange or impregnation techniques. The metal compounds which may be used for ion-exchange and/or impregnation may be compounds of any one of the following metals or groups of metals, namely those belonging to Groups IB, IIB, IIIA, IVA, VA, VIB, VIIB and VIII according to the Periodic Table due to Mendeleef. Specifically, compounds of copper, silver, zinc, aluminium, gallium, indium, thallium, lead, antimony, bismuth, chromium, molybdenum, tungsten, manganese, iron, cobalt, nickel, ruthenium, rhodium, palladium, iridium, platinum, rhenium, thorium and the rare earth metals are preferred.

The gallosilicate products of the present invention may be admixed or bound with other catalytic components or supports such as e.g. other zeolites or gallosilicates before or after impregnation or after exchange with one of the aforementioned metal compounds to produce an attrition resistant catalyst. The conventional alumina or silica binders may also be used.

The gallosilicates of the present invention may be used, whether or not impregnated and/or ion-exchnaged, admixed, supported or bound as catalysts for any of the following reactions: alkylation, dealkylation, dehydrocyclodimerisation, aromatisation, transalkylation, isomerisation, dehydrogenation, hydrogenation, cracking, hydrocracking, cyclisation, oligomerisation, polymerisation, and dehydration reactions, particularly dehydration of alcohols and athers. The gallosilicate catalysts may also be used for conversion of carbon monoxide/hydrogen mixtures to hydrocarbons. The gallosilicates may be used in the form of fixed, fluidised or moving beds.

The present invention is further illustrated with reference to the following Example.

TABLE A

| 2 theta | d-spacing | Relative intensity $100 \times I/I_o$ |
|---|---|---|
| 8.06 ± 0.2 | 11.25—10.70 | 50 to 100 |
| 10.06 ± 0.2 | 9.01—8.63 | 5 to 30 |
| 12.69 ± 0.2 | 7.09—6.87 | 10 to 30 |
| 16.28 ± 0.2 | 5.51—5.38 | 5 to 15 |
| 19.40 ± 0.2 | 4.62—4.53 | 5 to 15 |
| 20.26 ± 0.2 | 4.43—4.34 | 50 to 100 |
| 24.11 ± 0.2 | 3.72—3.66 | 50 to 100 |
| 24.52 ± 0.2 | 3.66—3.60 | 30 to 90 |
| 25.65 ± 0.2 | 3.50—3.45 | 15 to 45 |

Scanned up to 2 theta=32.

EXAMPLE 1

An aqueous solution of gallium nitrate containing 0.0215 moles of gallium was adjusted to a pH of about 6 using aqueous ammonia. The precipitate obtained was filtered and washed with distilled water and transferred into a basket containing aqueous sodium hydroxide solution (30 g, 0.0575 moles of sodium hydroxide). The mixture so formed was stirred until a clear solution was obtained. Diethanolamine (28 g ) was melted and added to the gallate solution and the resultant solution "A" was stirred at 20° C. for 10 minutes. 100 g of a commercial silica gel, (Ludox AS40) (Reg. Trade Mark) which contains 40% by weight of silica, was further diluted with 71 g of water and added to Solution A over a period of 15 minutes with vigorous stirring which was continued for a further 20 minutes. The resultant gel, composition 2.7Na$_2$O:24.8DEA:Ga$_2$O$_3$:62SiO$_2$:821-H$_2$O, was transferred to a stainless steel pressure vessel and crystallised at 175° C. for 48 hours. The product was filtered, washed and dried at 90° C.

The product was found by X-ray powder diffraction to be substantially crystalline with a diffraction pattern (Table 1) very similar to and consistent with the Theta-1 structure. It contained Si (41%). Ga (1.5%) and Na (1.4%).

TABLE 1

| 2-Theta | d | I/I$_o$ × 100 |
|---------|-------|-----|
| 8.06 | 11.0 | 100 |
| 10.06 | 8.79 | 17 |
| 12.69 | 6.98 | 16 |
| 16.28 | 5.45 | 10 |
| 19.40 | 4.58 | 10 |
| 20.26 | 4.38 | 65 |
| 24.11 | 3.691 | 61 |
| 24.52 | 3.361 | 44 |
| 25.65 | 3.473 | 21 |

Scanned up to 2 theta=32, peaks below I/I$_o$=5 not included. Intensity, as is known, changes with composition and pretreatment.

Comparative Test 1

A solution was prepared from a mixture of sodium aluminate (2.09 g), sodium hydroxide (1.68 g) and water (20 ml).

Diethanolamine (9.95 g) was melted and added to the solution and the resultant solution ("A") was stirred and maintained at 30° C. for 10 minutes with constant stirring.

66 g of a commercial silica gel, 'Ludox AS40' (Reg. Trade Mark) which contains 40% by weight of silica, was diluted with 40 ml of water to form solution "B". Thereafter solution "B" was added dropwise to solution "A" over a period of 40 minutes with constant stirring. Stirring was contiued for a further 20 minutes and then the resultant gel was transferred to an oven and crystallised at 170° C. for 93 hours in a revolving stainless steel pressure vessel.

The product was removed and found to contain substantially Theta-1 with a trace of MFI type zeolites (as defined in the "Atlas of Zeolite Structure Types" referred to above) and a little uncrystallised material, and it had an X-ray diffraction pattern as shown in Table 2. On calcination it was shown to contain Si (40.6% w/w), Al (1.34% w/w) and Na (0.87% w/w).

TABLE 2

| 2 theta | d-spacing | 100 × I/I$_o$ |
|---------|-----------|-----|
| 8.15 | 10.85 | 100 |
| 10.16 | 8.71 | 16 |
| 12.77 | 6.93 | 16 |
| 16.36 | 5.42 | 10 |
| 19.42 | 4.57 | 10 |
| 20.35 | 4.36 | 77 |
| 24.22 | 3.70 | 74 |
| 24.65 | 3.61 | 49 |
| 25.75 | 3.46 | 23 |
| 35.63 | 2.52 | 22 |

Diffraction peaks measured between 2 theta=4—36, peaks below I/I$_o$=5 not included.

Note that for nearly all cases the d-spacings of the X-ray powder diffraction pattern of gallo-Theta-1 (Table 1) are higher than those of alumino-Theta-1 (Table 2) as would be expected from the larger ionic and covalent radii of gallium compared to aluminium.

Comparative Test 2

A gel of composition 3.0Na$_2$O:32DEA:Ga$_2$O$_3$:30.0SiO$_2$:534H$_2$O was prepared in the same manner as that of Example 1. It was then transferred to a stainless steel pressure vessel and crystallised at 175° C. for 72 hours. The product was filtered, washed and dried at 90° C. The product was found by X-ray powder diffraction to be substantially crystalline with a diffraction pattern (Table 3) very similar to and consistent with the MFI structure. It was generally found that the d-spacings tend to be slightly larger in the MFI gallosilicate than the MFI aluminosilica the consistent with the larger covalent/ionic radius of gallium.

TABLE 3

| 2 theta | d | I/I$_o$ × 100 | 2 theta | d | I/I$_o$ × 100 |
|---------|-------|-----|---------|-------|-----|
| 7.64 | 11.57 | 100 | 22.80 | 3.901 | 71 |
| 8.54 | 10.36 | 56 | 22.97 | 3.872 | 48 |
| 8.78 | 10.07 | 18 | 23.43 | 3.796 | 27 |
| 12.92 | 6.85 | 7 | 23.65 | 3.762 | 34 |
| 13.64 | 6.49 | 10 | 24.13 | 3.689 | 20 |
| 14.48 | 6.12 | 13 | 26.67 | 3.343 | 7 |
| 15.22 | 5.82 | 8 | 28.98 | 3.081 | 8 |
| 15.62 | 5.67 | 10 | 29.57 | 3.021 | 10 |
| 20.08 | 4.42 | 7 | 29.69 | 3.009 | 10 |
| 20.54 | 4.32 | 8 | | | |

Scanned up to 2-theta=32, peaks below I/I$_o$=7 not included.

We claim:

1. A process for producing crystalline gallosilicates having the following composition in terms of the mole ratios of the oxides:

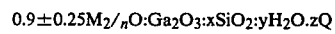

$$0.9\pm0.25M_{2/n}O:Ga_2O_3:xSiO_2:yH_2O.zQ$$

wherein M is at least one cation having a valence n, x is at least 10, y/x is from 0 to 30, Q is a template used in the synthesis of the gallosilicate and z/x is 0–20, wherein the gallosilicate in the organic free hydrogen-form has an X-ray diffraction pattern substantially as set forth in Table A of this specification, comprising freshly precipitating gallium hydroxide from a solution, dissolving the freshly precipitated gallium hydroxide in an aqueous alkali metal hydroxide solution, adding an organic or inorganic nitrogen base to the solution to form a mixture thereof, slowly adding a source of silica to the mixture of said freshly precipitated gallium hydroxide solution and the nitrogen base, mixing the solution until a homogeneous gel is formed, and crystallising the gel at a temperature above 70° C. to obtain said crystalline gallosilicate.

2. A process according to claim 1 wherein the cation M is the gallo-silicate is selected from H$^+$, ammonium, alkali metal cations, alkaline earth metal cations, organic nitrogen containing cations, aluminium cation, gallium cation and mixtures thereof.

3. A process according to claim 1 or 2 wherein the cations present in the gallo-silicate are replaced using ion exchange techniques either wholly or partially by hydrogen ions or metal cations.

4. A process according to claim 1 wherein the silica to gallia mole ratio in the mixture is at least 10:1.

5. A process according to claim 1 or 4 wherein the free alkali metal(s) hydroxide to water mole ratio is greater than $2\times10^{-3}$:1.

6. A process according to claim 1 wherein the mole ratio of water to silica is less than 100:1.

7. A process according to claim 1 wherein the nitrogen containing base is selected from ammonia and the alkanolamines and their decomposition products under the synthesis conditions.

8. A process according to claim 1, wherein the mole ratio of silica to free alkali metal(s) hydroxide is greater than 1:1.

9. A process according to claim 1,
wherein the silica to gallia mole ratio in the mixture is at least 10:1,
wherein the free alkali metal(s) hydroxide to water mole ratio is greater than $2\times10^{-3}$:1,
wherein the silica to free alkali metal(s) hydroxide mole ratio is greater than 1:1, and
wherein the water to silica mole ratio is less than 100:1.

10. A process as claimed in claim 1,
wherein the silica to gallia mole ratio in the mixture is greater than 40:1,
wherein the free alkali metal(s) hydroxide to water mole ratio is in the range $2\times10^{-3}$:1 to $8\times10^{-3}$:1,
wherein the silica to free alkali metal(s) hydroxide mole ratio is between 5:1 and 80:1, and
wherein the water to silica mole ratio is between 6:1 and 30:1.

11. A process as claimed in claim 1,
wherein the silica to gallia mole ratio is in the range 60:1 to 500:1,
wherein the free alkali metal(s) hydroxide to water mole ratio is in the range $2\times10^{-3}$:1 to $8\times10^{-3}$:1,
wherein the silica to free alkali metal(s) hydroxide mole ratio is between 5:1 and 40:1, and
wherein the water to silica mole ratio is between 9:1 and 30:1.

* * * * *

UNITED STATES PATENT AND TRADEMARK OFFICE
CERTIFICATE OF CORRECTION

PATENT NO. : 4,585,641
DATED : April 29, 1986
INVENTOR(S) : SAMI A.I. BARRI AND DENNIS YOUNG It is certified that error appears in the above-identified patent and that said Letters Patent are hereby corrected as shown below:

Col. 6, line 61, "basket" should read --beaker--

Col. 7, Table 1, Under "d", "3.361" should read --3.631--

In The Claims:

Col. 8, line 61 claim 2, "is the gallo-silicate" should read --in the gallo-silicate--

Signed and Sealed this

Twenty-sixth Day of August 1986

[SEAL]

Attest:

DONALD J. QUIGG

Attesting Officer

Commissioner of Patents and Trademarks